United States Patent [19]

Bielefeldt et al.

[11] Patent Number: 5,059,711
[45] Date of Patent: Oct. 22, 1991

[54] PROCESS FOR THE PREPARATION OF TRIFLUOROMETHANESULPHONIC ACID

[75] Inventors: Dietmar Bielefeldt, Ratingen; Albrecht Marhold, Leverkusen, both of Fed. Rep. of Germany

[73] Assignee: Bayer Aktiengesellschaft, Leverkusen, Fed. Rep. of Germany

[21] Appl. No.: 172,732

[22] Filed: Mar. 24, 1988

[30] Foreign Application Priority Data

Apr. 11, 1987 [DE] Fed. Rep. of Germany ....... 3712318

[51] Int. Cl.$^5$ .......................................... C07C 303/00
[52] U.S. Cl. .................................................. 562/113
[58] Field of Search ....................... 260/513 R, 513 F; 562/113

[56] References Cited

U.S. PATENT DOCUMENTS 2,884,453 4/1959 Tulleck et al. .
3,948,922 4/1976 Lowe ................................. 260/513 R
4,012,453 3/1977 Nychka et al. .
4,052,468 10/1977 Peterson et al. .
4,052,470 10/1977 Nychka et al. .
4,060,555 11/1977 Peterson et al. .
4,105,691 8/1978 Sweeney et al. .
4,239,696 12/1980 Schreyer et al. ............... 260/513 R

FOREIGN PATENT DOCUMENTS 1232954 3/1967 Fed. Rep. of Germany .
2658139 6/1977 Fed. Rep. of Germany .

OTHER PUBLICATIONS

Haszeldine, R. N., and Kidd, J. M., *J. Chem. Soc.*, (London), (1955), p. 3871.
Japanese Published Specification (JP-OS) 85-243,061.
Howells, R. D., and McCown, J. D., *Trifluoromethanesulfonic Acid and Derivatives*, Chemical Reviews, 77, 69-92, (1977).
Dear, R. E., and Gilbert, E., *Synthesis*, 6, 310.
Haszeldine and Kidd, *J. Chem. Soc.*, (1954), pp. 4228-4232.
Tullock and Coffman, "Synthesis of Fluorides by Metathesis with Sodium Fluoride", *J. Org. Chem.*, 25, 2016, (1960).

Primary Examiner—Alan Siegel
Attorney, Agent, or Firm—Sprung Horn Kramer & Woods

[57] ABSTRACT

Trifluoromethanesulphonic acid is prepared from bis-(trifluoromethyl) disulphane in the liquid phase and in acidic medium by means of an oxygen-containing oxidizing agent.

8 Claims, No Drawings

PROCESS FOR THE PREPARATION OF TRIFLUOROMETHANESULPHONIC ACID

The present invention relates to a process for the preparation of trifluoromethanesulphonic acid bis-(trifluoromethyl) disulphane.

Trifluoromethanesulphonic acid is a universally utilizable chemical, which is required, for example for the preparation of plant protection agents (see JP-OS (Japanese Published Specification) 85-243,061) and can be employed as an acylation catalyst (see Chem. Reviews, 77, 69–92 (1977)).

According to the only known process which yields trifluoromethanesulphonic acid commencing from disulphides, di-(dichlorofluoromethyl) disulphide is reacted with hydrogen fluoride and oxygen in the gas phase at 340 to 410° C. in the presence of Deacon catalysts, which are generally oxides or halides of polyvalent metals having variable valency states (see DE-OS (German Published Specification) 2,658,139, in particular Example 195). The high temperatures to be used, the corrosion problems occurring on use of hydrogen fluoride and oxygen, the production of trifluoromethanesulphonic acid as a mixture with difluoromonochloro- and monofluorodichloromethanesulphonic acid, the lack of information about the absolute and relative amounts in which trifluoromethanesulphonic acid has been obtained and the lack of information about whether and if necessary how trifluoromethanesulphonic acid can be isolated from the reaction mixture, are disadvantageous in this process.

A process has now been found for the preparation of trifluoromethanesulphonic acid which is characterized in that bis-(trifluoromethyl) disulphane is treated in the liquid phase and in acidic medium with an oxygen-containing oxidizing agent.

The bis-(trifluoromethyl) disulphane required as the starting product for the process according to the invention is known and is accessible in a simple manner. It is obtained, for example, as a hitherto undesired by-product in the preparation of $CF_3SCl$ (see W. Tullock and D.D. Coffmann, J. org. Chem., 25, 2016 (1960)) by fluorination of trichloromethylsulphenyl chloride by means of sodium fluoride (see U.S. Pat. No. 2,884,453) or by fluorination of bis-(trichloromethyl disulphide) by means of hydrogen fluoride (see DE-OS (German Published Specification) 1,232,954 and Synthesis 6, 310 (1972)).

The liquid phase necessary according to the invention and the acid medium necessary according to the invention can be verified for example, by carrying out the reaction in the presence of a strong acid which is liquid under the reaction conditions used. This acid is preferably anhydrous or low in water. Suitable acids are, for example, sulphuric acid in concentrations of 70 to 100% by weight, oleum containing 0 to 100% by weight of free $SO_3$, phosphoric acid in concentrations of 85 to 100% by weight and acetic acid in concentrations of 90 to 100% by weight, as well as fluorine-containing organic and inorganic acids such as fluoroacetic acids, in particular trifluoroacetic acid, perfluoroalkanesulphonic acids and fluorosulphonic acid. Mixtures of several acids can also be employed.

The amount of acid is not critical. For example, 5 to 20 parts by weight of acid can be employed per part by weight of bis-(trifluoromethyl) disulphane.

The oxygen-containing oxidizing agents to be employed according to the invention can be of various types. For example, suitable substances for this are those which contain peroxidic oxygen, for example hydrogen peroxide, inorganic peracids, such as Caro's acid ($H_2SO_5$), or salts thereof, organic peracids, such as aliphatic $C_1$-to $C_4$-peracids and, optionally substituted, aromatic percarboxylic acids, peroxo salts, such as peroxo-sulphates and peroxoborates, or sulphur peroxocompounds substituted by fluorine, such as $S_2O_6F_2$. Suitable oxygen-containing oxidizing agents are also other active oxygen-containing compounds, for example ozone. Other oxygen-liberating and/or oxygen-transferring compounds can also be employed, for example nitric acid, nitrates, oxides of metals in higher valency states, the corresponding acids and the corresponding salts. Molecular oxygen can also be employed, in particular together with catalysts and/or activators.

It can be advantageous to employ the oxygen-containing oxidizing agent together with a catalyst, for example nitric acid or aqua regia and vanadium pentoxide, or molecular oxygen and osmium tetroxide, or a peroxocompound and a heavy metal salt.

The following oxidants are preferably employed: hydrogen peroxide, peracetic or perpropionic acid, preferably dissolved in water or an inert organic solvent, perbenzoic acid, 3-chloro-perbenzoic acid, peroxosulphates, peroxodisulphates, and Caro's acid.

Hydrogen peroxide, Caro's acid and peroxodisulphates are particularly preferred oxidizing agents.

It is not imperative that the oxygen-containing oxidizing agents employed react with bis-(trifluoromethyl) disulphane in the form employed; instead they can be converted wholly or partly into other oxygen-containing oxidizing agents before this reaction. For example, Caro's acid can be formed from hydrogen peroxide and sulphuric acid, a nitrosyl ion-containing mixture (=so-called aqua regia) can be formed from nitric acid and hydrochloric acid or peracetic acid can be formed from hydrogen peroxide and acetic acid.

Similarly, the oxygen-containing oxidizing agent desired in each case can also be formed in situ, for example. Caro's acid from hydrogen peroxide and sulphuric acid.

The amount of the oxygen-containing oxidizing agent can be varied within a wide range. For example, 2 to 20 equivalents of oxidizing agent per mol of bis-(trifluoromethyl) disulphane are suitable. This amount is preferably 5 to 10 equivalents of oxidizing agent per mol of bis-(trifluoromethyl) disulphane.

The process according to the invention can, for example, be carried out at temperatures from −20 to 100° C. Preferably, the temperatures are in the range of from 0 to 60° C.

The process according to the invention is generally carried out at atmospheric pressure. However, if it is wished to work at reaction temperatures at which some or all components of the reaction mixture are volatile, then the reaction is expediently carried out under increased pressure, for example in closed vessels or with inert gas pressurization. If the volatility of the reaction mixture allows, the reaction can also be carried out at reduced pressures. Due to practical considerations, a pressure range of 1 to 6 bar is advantageously maintained.

The process according to the invention can be carried out in the presence or in the absence of solvents. Suitable solvents are, for example, perfluorinated ethers and sulphones, such as tetramethylene sulphone.

Solvents can be added to the reaction mixture as such, but also by employing one or more of the materials required for the process according to the invention in the form of a solution.

It is advantageous to minimize the amount of water in the reaction mixture, in particular in the absence of solvents. The reaction therefore preferably commences from a starting mixture which is as anhydrous as possible and it is attempted, if appropriate, to remove or make inactive water formed during the reaction, for example by addition of sulphur trioxide when working in a sulphuric acid medium or by addition of phosphorus pentoxide when working in phosphoric acid.

Suitable reaction times for the process according to the invention are, for example, those in the range of 2 to 72 hours.

After carrying out the process according to the invention, trifluoromethanesulphonic acid can be recovered from the reaction mixture, for example by distillation. This can be accomplished by initially dehydrating and then distilling the reaction mixture.

Using the process according to the invention, it is possible to obtain trifluoromethanesulphonic acid in a simple manner in good purities and with advantageous yields. The process according to the invention is furthermore distinguished in that it can be carried out at relatively low temperatures and in that it is advantageous with respect to corrosion problems and energy costs. Moreover, it allows the preparation of trifluoromethanesulphonic acid on an industrial scale from a starting product for which, hitherto, no industrial utility is known.

It is extremely surprising that the advantages mentioned can be obtained using the process according to the invention, since in J. Chem. Soc. 4230 (1954) it is described that, on attempting the oxidation of bis-(trifluoromethyl) disulphide by means of concentrated nitric acid, no reaction occurred and at high temperatures only unidentified decomposition products are found.

The following examples illustrate the process according to the invention without limiting it thereto.

EXAMPLES

Example 1

220 g (1.1 mol) of $CF_3SSCF_3$ were added at 20° C. to 540 g (2 mol) of potassium peroxodisulphate dissolved in 1,000 ml of sulphuric acid of density 1.832 (at 20° C.). The reaction mixture was stirred at 40° C. for 16 hours. The reaction mixture was then subjected to a distillation. Initially, 86 g (0.43 mol) of unreacted $CF_3SSCF_3$ were recovered. 44 g (19% of theory) of trifluoromethanesulphonic acid of boiling point 80° C. at a pressure of 0.5 mbar were then obtained. The product obtained had a refractive index $n^{20}_D = 1.341$ and an $^{19}F$-NMR spectrum having a characteristic signal at $\delta = -0.3$ ppm (measured using $CF_3CO_2H$ as external standard). The melting point of the N-anilinotrifluoromethanesulphonate prepared from the trifluoromethanesulphonic acid thus obtained was 268° C. No melting point depression was found using N-anilinotrifluoromethanesulphonate prepared from commercial trifluoromethanesulphonic acid.

Example 2

820 g (12.1 mol) of 50% strength aqueous hydrogen peroxide were added at between 20 and 40° C. to 405 g (2.0 mol) of $CF_3SSCF_3$, which were dissolved in 2,000 ml of sulphuric acid of density 1.840 (at 15° C.). After the addition was complete the mixture was stirred at 20 to 25° C. overnight and then 76 g (0.38 mol) of unreacted $CF_3SSCF_3$ were removed by distillation. The product mixture remaining was rendered anhydrous by addition of 4,900 g of 65% strength by weight oleum. Following this, trifluoromethanesulphonic acid was removed by distillation and 775 g of crude product were collected in a boiling range of 20 to 90° C. at 400 mbar. Anhydrous trifluoromethanesulphonic acid was obtained by a further distillation through a 30 cm Vigreux column. The yield was 260 g (=52% of theory). The boiling point of the trifluoromethanesulphonic acid thus isolated was 58 to 59° C. at 22 mbar. The $^{19}F$-NMR spectrum showed a characteristic signal at $\delta = -0.1$ ppm (measured using $CF_3CO_2H$ as external standard).

Example 3

836 g of a mixture containing 86 g of trifluoromethanesulphonic acid (obtained by Example 2) and 750 g of 86% strength sulphuric acid were added to 280 g (2.0 mol) of phosphorus pentoxide. Following this, anhydrous trifluoromethanesulphonic acid was distilled from the mixture. At a pressure of 18 mbar, 44 g of anhydrous trifluoromethanesulphonic acid were isolated at 63 to 67° C. This corresponds to 51% of theory, with reference to reacted $CF_3SSCF_3$.

Example 4

280 g (4.1 mol) of 50% strength aqueous hydrogen peroxide were added with ice cooling to a solution of 200 g (1.0 mol) of $CF_3SSCF_3$ and 1,000 g (12.5 mol) of $SO_3$ in (1.0 mol) of $CF_3SSCF_3$ and 1,000 g (12.5 mol) of $SO_3$ in 1,437 g of 96% strength by weight sulphuric acid. The reaction mixture was stirred at 20° C. for another 2 hours and the volatile constituents were then separated off by distillation. Redistillation of the volatile constituents thus separated off gave 52 g (0.35 mol) of anhydrous trifluoromethanesulphonic acid of boiling point 59 to 63° C. at 20 mbar. This corresponds to a yield of 26% of theory with reference to hydrogen peroxide.

We claim:

1. A process for the preparation of trifluoromethanesulphonic acid, comprising reacting bis-(trifluoromethyl)disulphane in the liquid phase and in an acidic medium with an oxygen-containing oxidizing agent selected from the group consisting of an inorganic peracid, a salt of an inorganic peracid, an organic peracid, a peroxo salt, a sulphur-peroxo compound substituted with fluorine, an active oxygen-containing compound, an oxide of a metal in a higher valency state, a corresponding acid, a corresponding salt and molecular oxygen, wherein 5 to 20 parts by weight of acid are employed per part by weight of bis-(tri-fluoromethyl) disulphane and wherein said reacting is carried out at a temperature of −20° C. to 100° C.

2. A process according to claim 1, in which the reaction is carried out in the presence of a strong acid which is liquid under the reaction conditions.

3. A process according to claim 2, in which the acid is anhydrous.

4. A process according to claim 2, in which the acid is low in water.

5. A process according to claim 1, in which hydrogen peroxide, peracetic acid, perpropionic acid, perbenzoic acid, 3-chloro-perbenzoic acid, a peroxosulphate, a peroxodisulphate or Caro's acid are employed as oxidizing agent.

6. A process according to claim 1, in which 2 to 20 equivalents of the oxidizing agent are employed per mol of bis-(trifluoromethyl) disulphane.

7. A process according to claim 1, in which the reaction is carried out at pressures of 1 to 6 bar.

8. A process according to claim 1, in which trifluoromethane-sulphonic acid is recovered by distillation from the reaction mixture present after the treatment with the oxygen-containing oxidizing agent.

* * * * *